United States Patent [19]

McCully

[11] Patent Number: 4,618,685

[45] Date of Patent: Oct. 21, 1986

[54] N-HOMOCYSTEINE THIOLACTONYL RETINAMIDE AND USE THEREOF AS AN ANTINEOPLASTIC AGENT

[76] Inventor: Kilmer S. McCully, 15 Wildwood St., Winchester, Mass. 01890

[21] Appl. No.: 810,175

[22] Filed: Dec. 18, 1985

[51] Int. Cl.[4] .................. C07D 333/36; A61K 31/38
[52] U.S. Cl. ...................................................... 549/63
[58] Field of Search ......................................... 549/63

[56] References Cited

U.S. PATENT DOCUMENTS 4,255,443  3/1981  McCully .
4,383,994  5/1983  McCully .

OTHER PUBLICATIONS

Bollag, The Lancet, pp. 860–863, Apr. 16, 1983.
du Vigneaud, et al., Journal of Biological Chemistry, 126:217–231, 1938.
McCully and Ragsdale, The Am. J. of Pathology, 61(1):1–8, Oct. 1970.
Moon, et al., The Retinoids, vol. 2, pp. 327–371, Academic Press, 1984.
Spindel et al., Biochimica et Biophysica Acta, 343:687–691, 1974.
McCully et al., Atherosclerosis, 22:215–227, 1975.
McCully et al., Chemotherapy, 23:44–49, 1977.

*Primary Examiner*—Alan Siegel
*Attorney, Agent, or Firm*—John S. Roberts, Jr.

[57] ABSTRACT

This invention is concerned with a new compound, useful to reduce tumors in laboratory animals, having the following structural formula:

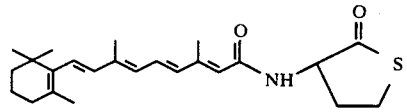

The compound is prepared by reacting the free base of homocysteine thiolactone with all trans retinoic acid in the presence of dicyclohexylcarbodiimide as a dehydrating agent as follows:

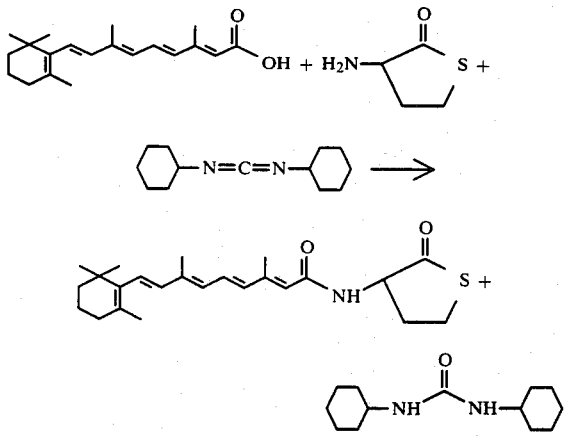

The reaction is carried out in a suitable non-polar solvent. The compound may also be used to agglutinize human blood platelets.

1 Claim, No Drawings

N-HOMOCYSTEINE THIOLACTONYL RETINAMIDE AND USE THEREOF AS AN ANTINEOPLASTIC AGENT

The purpose of this invention is to provide a new and novel compound, N-homocysteine thiolactonyl retinamide containing normal biochemical constituents, retinoic acid and homocysteine thiolactone, which has shown utility in decreasing the growth of malignant neoplasms in animals.

The literature prior art is cited below:

W. Bollag "Vitamin A and Retinoids: From Nutrition to Pharmacotherapy in Dermatology and Oncology." The Lancet, p. 860–863, Apr. 16, 1983.

Vincent du Vigneaud, Wilbur I. Patterson, Madison Hunt "Opening of the Ring of the Thiolactone of Homocysteine". Journal of Biological Chemistry, 126:217–231, 1938.

Kilmer S. McCully and Bruch C. Ragsdale, "Production of Arteriosclerosis by Homocysteinemia", The American Journal of Pathology, Vol. 61, No. 1, pp. 1–8, October 1970.

Richard C. Moon and Loretta M. Itri, "Retinoids and Cancer", The Retinoids, Vol. 2, pp. 327–371, Academic Press, 1984.

Kilmer S. McCully, "Homocysteine Metabolism in Scurvy, Growth and Arteriosclerosis", Nature, 231:391–392, July 17, 1971.

Kilmer S. McCully, "Homocysteinemia and Arteriosclerosis", American Heart Journal, 83:571–573, April 1971.

Elliott Spindel and Kilmer S. McCully "Conversion of Methionine to Homocysteine Thiolactone in Liver, Biochimica et Biophysica Acta, 343:687–691, 1974.

Kilmer S. McCully and Robert B. Wilson, "Homocysteine Theory of Arteriosclerosis", Atherosclerosis, 22:215–227, 1975.

Kilmer S. McCully and Peter Clopath, "Homocysteine Compounds Which Influence the Growth of a Malignant Neoplasm, Chemotherapy", 23:44–49, 1977.

Other prior art includes Kilmer S. McCully, U.S. Pat. No. 4,255,443 directed to "Homocysteine Thiolactone Perchlorate as a Tumor Promoter," Mar. 10, 1981; Kilmer S. McCully, U.S. Pat. No. 4,383,994, directed to N-homocysteine thiolactone derivatives, useful as antineoplastic agents. U.S. Pat. Nos. 4,072,703 "Thiol Esters of Homocysteine" and 3,068,242 are of interest.

BACKGROUND

An abnormality of homocysteine thiolactone metabolism occurs in cultured malignant cells, as reported in Cancer Research 36:3198–3202, 1976. As a result of this abnormality homocysteine thiolactone reacts with protein amino groups, forming homocysteinyl peptide bonds and a free sulfhydryl group, a process known as thiolation. It was suggested that normal cells contain an N-substituted derivative of homocysteine thiolactone which prevents thiolation of proteins by homocysteine thiolactone, thereby preventing the malignant growth state characteristic of cancer cells. Certain N-substituted derivatives of homocysteine thiolactone, composed of normal biochemical constituents, pyridoxal and arachidonic acid, modify the growth of malignant neoplasms in mice, as reported in Chemotherapy 23:44–49, 1977. Several other N-substituted derivatives of homocysteine thiolactone, as taught in U.S. Pat. No. 4,383,994, consisting of N-maleyl homocysteine thiolactone amide, N-maleamide homocysteine thiolactone amide, oxalyl homocysteine thiolactone perchlorate, and rhodium trichloride oxalyl homocysteine thiolactone, decrease the growth of malignant neoplasms in animals. Encapsulation of N-maleamide homocysteine thiolactone amide within liposomes enhances its antineoplastic activity, as reported in Proceedings of the Society for Experimental Biology and Medicine, 180:57–61, 1985. Administration of rhodium trichloride oxalyl homocysteine thiolactone in a solution of mixed lipids enhances its antineoplastic activity (unpublished manuscript, 1985).

Retinoids, natural and synthetic compounds related to vitamin A (retinol), have been known for many years to modify the differentiation and growth characteristics of malignant neoplasms. In addition, retinoids are active in preventing the development of malignant neoplasms induced in animals by a variety of carcinogens. For a discussion of these biological characteristics of retinoids, see R. C. Moon and L. M. Itri, "Retinoids and Cancer" in The Retinoids, Volume 2, pp 327–372, Academic Press, 1984. Retinoic acid, the acid derivative of retinol, for example, is active in preventing the development of urinary bladder cancer in rats induced by carcinogens. A major disadvantage of the use of retinoids, including retinoic acid, for chemoprevention or chemotherapy of cancer is that these compounds exhibit marked cumulative toxicity, manifested by the hypervitaminosis A syndrome, as reviewed by W. Bollag, Lancet 1:860–863, 1983. The toxicity of retinoids has limited their usefulness in clinical trials of chemotherapeutic activity.

Homocysteine thiolactone is a product of methionine metabolism in liver, as reported in Biochimica et Biophysica Acta 343:687–691, 1974. A part of the homocysteine thiolactone produced by metabolism of methionine is bound to the lipids of liver cells. Homocysteine thiolactone hydrochloride produces atherosclerotic lesions in the arteries of experimental animals when injected parenterally, as reported in American Journal of Pathology 61:1–11, 1970. Homocysteine thiolactone perchlorate causes atherosclerotic lesions when fed in an experimental diet to animals, as reported in Atherosclerosis 22:215–227, 1975. Homocysteine thiolactone perchlorate, as taught in U.S. Pat. No. 4,255,443, affects the growth of malignant tumors. Homocysteine thiolactone free base is a reactive substance which is soluble in non-polar solvents and spontaneously dimerizes to the corresponding diketopiperazine derivative, as reported in Journal of Biological Chemistry 126:217–231, 1938.

Cyclophosphamide is an example of a commonly employed antineoplastic compound which has the disadvantage of cumulative toxicity after prolonged administration in cancer chemotherapy. The subject compound of this invention, N-homocysteine thiolactonyl retinamide, overcomes the disadvantage of toxicity of chemotherapeutic compounds and retinoids, because it is composed of retinoic acid and homocysteine thiolactone in a chemical form which prevents toxicity to normal cells and tissues. Because large doses of N-homocysteine thiolactonyl retinamide can be given without toxicity, the compound is useful for chemoprevention and chemotherapy of malignant neoplasms in animals.

DESCRIPTION OF THE INVENTION

The subject compound of this invention may be represented by the following structural formula:

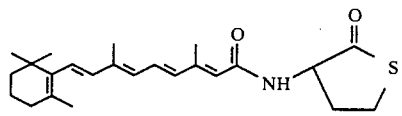

N-homocysteine thiolactonyl retinamide The subject compound is formed by the reaction of the free base of homocysteine thiolactone with all trans retinoic acid in the presence of dicyclohexylcarbodiimide as dehydrating agent:

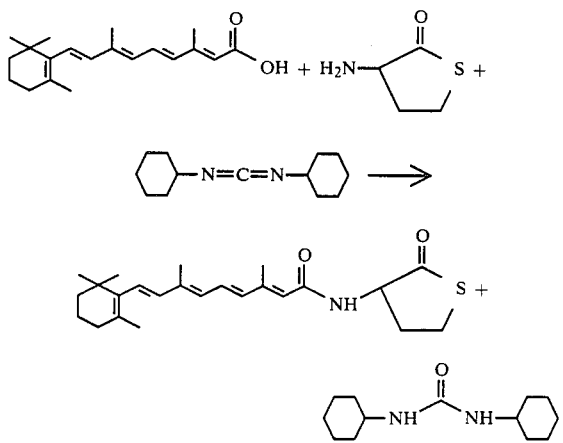

The reaction is carried out in a suitable non-polar solvent, such as tetrahydrofuran. N-homocysteine thiolactonyl retinamide is separated from dicyclohexylurea by partition between ethyl acetate and water, separation of the ethyl acetate, drying and evaporation of the solvent. The resulting yellow powder is soluble in organic solvents such as ethyl acetate, ethanol, chloroform and methylene chloride. Recrystallization can be carried out conveniently in ethyl acetate or ethanol.

The process of preparing N-homocysteine thiolactonyl retinamide is presented in Example 1, below:

EXAMPLE 1

To prepare the free base of homocysteine thiolactone, dissolve 1.01 g of sodium hydroxide in 25 ml water, add 100 ml of methylene chloride, and with rapid mixing, add 3.84 g of homocysteine thiolactone hydrochloride slowly. After 15 minutes of mixing, separate the methylene chloride layer, dry over anhydrous sodium sulfate and evaporate the solvent under reduced pressure at 37° C. 1.17 g (10 mmoles) of the resulting clear liquid (homocysteine thiolactone free base) is immediately added to 50 ml of tetrahydrofuran containing 3.00 g (10 mmoles) of all trans retinoic acid. 2.06 g (10 mmoles) of dicyclohexylcarbodiimide is added, and the reaction mixture is stirred 16 hours at 20° C., protected from light. The tetrahydrofuran is removed at 37° C. under reduced pressure, and the yellow-white residue is added to 500 ml of water and 500 ml of ethyl acetate. The mixture is stirred vigorously for one hour, and the ethyl acetate layer is separated and dried over anhydrous sodium sulfate. The ethyl acetate is concentrated to about 20 ml at 50° C. under reduced pressure and cooled. 2.75 g of yellow powder (N-homocysteine thiolactonyl retinamide) represents 69% of theoretical yield. m.p. 172° C. Analysis: C, calculated, 72.2; found, 71.99, corresponds to $C_{24}H_{33}NSO_2$. NMR 60 MHz multiplets 1.1–2.2, triplet 6.3, singlet 7.2 ppm.

In addition to tetrahydrofuran as a solvent, other non-polar solvents may be employed.

Having described the compound and its method of preparation, it is now important to consider the effect of N-homocysteine thiolactonyl retinamide on the growth of malignant neoplasms.

EXAMPLE 2

The effect is shown of the subject compound on growth of a malignant tumor in C57 B1/6N male mice with transplanted MU04 rhabdomyosarcoma. The compound was dissolved or suspended in dimethylsulfoxide, liposomes (comprised of aqueous buffer and the lipids, phosphatidyl choline, cholesterol and stearlamine in molar ratios of 4:3:1), mixed lipids (comprised of phosphatidyl choline, cholesterol and cholesteryl palmitate in molar ratios of 1:1:1) with triolein, or triolein, and injected twice weekly intraperitoneally for 10–14 days after tumor transplantation.

The subcutaneous neoplasms were dissected and weighed with the results shown in Table I. NHTR is N-homocysteine thiolactonyl retinamide of the invention.

TABLE 1

| Dose of NHTR mg/kg/day | Days treated | Vehicle | Survivors total | Tumor weight g + S.D. | P |
|---|---|---|---|---|---|
| — | 14 | liposomes | 24/25 | 1.84 ± 0.77 | — |
| 35 | 14 | lipsomes | 24/25 | 1.19 ± 0.65 | 0.0009 |
| 35 | 14 | dimethyl-sulfoxide | 25/25 | 1.17 ± 0.52 | 0.0002 |
| — | 11 | mixed lipids | 20/20 | 0.60 ± 0.25 | — |
| 100 | 11 | mixed lipids | 15/20 | 0.17 ± 0.18 | 0.0000001 |
| — | 10 | triolein | 18/18 | 0.60 ± 0.27 | — |
| 100 | 10 | triolein | 14/18 | 0.35 ± 0.19 | 0.003 |

The P values were calculated for differences between control and experimental groups, using the student t test. The data show that N-homocysteine thiolactonyl retinamide decreased the growth of a malignant neoplasm in mice.

N-homocysteine thiolactonyl retinamide toxicity was determined by intraperitoneal injection in mice as shown in Example 3, below:

EXAMPLE 3

N-homocysteine thiolactonyl retinamide toxicity was determined by intraperitoneal injection in C57 B1/6N male mice without transplanted tumors. The compound (262 mg) was dissolved in 25 ml of methylene chloride:-methanol (4:1 by vol), containing triolein (10 ml), phosphatidyl choline (247 mg), cholesterol (116 mg) and cholesteryl palmitate (187 mg). The solvents were evaporated under reduced pressure at 50° C. 10 ml of methylene chloride was added, and the solvent was again evaporated under reduced pressure at 50° C. 0.5 ml of the yellow oily solution was injected intraperitoneally. The results of this test for toxicity are shown in Table 2.

TABLE 2

| Dose of NHTR mg/kg/day | Total dose g/kg | Days treated | Body weight g | Survivors/ total | Condition |
|---|---|---|---|---|---|
| 400 | 1.6 | 4 | 32.5 | 10/10 | good |

These data show that a solution of N-homocysteine thiolactonyl retinamide in mixed lipids is tolerated satisfactorily in large dose over a period of 4 days.

The effect of N-homocysteine thiolactonyl retinamide on aggregation of platelets was demonstrated on normal human blood as shown in Example 4 below:

EXAMPLE 4

To demonstrate the effect of N-homocysteine thiolactonyl retinamide on platelets, 35 ml of normal human blood was anticoagulated, centrifuged and the platelet rich fraction of plasma was separated. Using an aggregometer, the platelets were shown to aggregate normally in the presence of collagen or thrombin. The subject compound, retinoic acid, and homocysteine thiolactone free base, prepared according to the procedure in Example 1, were dissolved in chloroform and added to platelets. As controls, homocysteine thiolactone hydrochloride, homocysteine thiolactone perchlorate and homocysteine were dissolved in water and added to platelets. The following results were obtained as seen in Table 3.

TABLE 3

| Compound added | Final concentration (mcg/ml) | Primary aggregation |
|---|---|---|
| N—homocysteine thiolactonyl retinamide | 10 | + |
| All trans retinoic acid | 10 | + |
| homocysteine thiolactone free base | 10 | + |
| homocysteine thiolactone hydrochloride | 10 | − |
| homocysteine thiolactone perchlorate | 10 | − |
| homocysteine | 10 | − |
| (chloroform only) | — | − |

These results show that N-homocysteine thiolactonyl retinamide, all trans retinoic acid, and homocysteine thiolactone free base cause primary aggregation of human platelets.

The compound herein disclosed and claimed has been found effective in diminishing the size of tumors in laboratory mice and effective in aggregating human platelets. Based on studies with laboratory animals it may be possible, through further study, to find that the compound may have value as a therapeutic agent in the treatment and prevention of human cancer and it may also be possible to demonstrate the use of this compound to treat and prevent human arteriosclerosis.

I claim:
1. N-homocysteine thiolactonyl retinamide.

* * * * *